United States Patent
Cumming

(10) Patent No.: US 9,585,745 B2
(45) Date of Patent: Mar. 7, 2017

(54) FOLDABLE INTRAOCULAR LENS WITH RIGID HAPTICS

(71) Applicant: James Stuart Cumming, Laguna Beach, CA (US)

(72) Inventor: James Stuart Cumming, Laguna Beach, CA (US)

(*) Notice: Subject to any disclaimer, the term of this patent is extended or adjusted under 35 U.S.C. 154(b) by 0 days.

(21) Appl. No.: 15/132,489

(22) Filed: Apr. 19, 2016

(65) Prior Publication Data

US 2016/0262871 A1 Sep. 15, 2016

Related U.S. Application Data

(63) Continuation of application No. 14/143,612, filed on Dec. 30, 2013, now abandoned, and a continuation-in-part of application No. 13/017,189, filed on Jan. 31, 2011, and a continuation-in-part of application No. 14/257,933, filed on Apr. 21, 2014, now Pat. No. 9,351,825, which is a continuation-in-part of application No. 14/143,612, filed on Dec. 30, 2013, now abandoned, application No. 15/132,489, which is a continuation-in-part of application No. 14/274,352, filed on May 9, 2014, now abandoned, which is a continuation of application No. 13/472,893, filed on May 16, 2012, now Pat. No. 8,734,512, application No. 15/132,489, which is a continuation-in-part of application No. 14/541,188, filed on Nov. 14, 2014, which is a (Continued)

(51) Int. Cl.
*A61F 2/16* (2006.01)

(52) U.S. Cl.
CPC ............. *A61F 2/16* (2013.01); *A61F 2/1613* (2013.01); *A61F 2/1624* (2013.01); *A61F 2/1629* (2013.01); *A61F 2002/169* (2015.04); *A61F 2002/1681* (2013.01); *A61F 2002/1682* (2015.04); *A61F 2002/1689* (2013.01); *A61F 2002/1696* (2015.04); *A61F 2230/0006* (2013.01); *A61F 2230/0069* (2013.01)

(58) Field of Classification Search
CPC .... A61F 2/1648; A61F 2/1613; A61F 2/1635; A61F 2/1629; A61F 2/1694; A61F 2002/1681; A61F 2002/1689
See application file for complete search history.

(56) References Cited

U.S. PATENT DOCUMENTS

| 2,834,023 A | 5/1958 | Lieb |
| 4,073,014 A | 2/1978 | Poler |

(Continued)

FOREIGN PATENT DOCUMENTS

| CA | 2110184 A1 | 12/1992 |
| CH | 681687 | 5/1993 |

(Continued)

OTHER PUBLICATIONS

International Search Report and Written Opinion for PCT/US2014/057037 dated Jan. 20, 2015 in 12 pages.
Davison, J.A., Chapter 11: Intraocular Lenses, *Duane's Clinical Ophthalmology on CD-ROM*, Lippincott Willliams & Wilkins, 2005, vol. 6, pp. 1-46.
International Search Report and Written Opinion for PCT/US2014/072518 dated Jul. 23, 2015 in 15 pages.

(Continued)

*Primary Examiner* — David H. Willse
*Assistant Examiner* — Tiffany Shipmon
(74) *Attorney, Agent, or Firm* — Sheppard, Mullin, Richter & Hampton LLP

(57) ABSTRACT

An intraocular lens comprises a flexible optic and at least one haptic connected to the optic. The at least one haptic comprises a rigid structure.

28 Claims, 4 Drawing Sheets

Related U.S. Application Data continuation-in-part of application No. 14/257,933, filed on Apr. 21, 2014, now Pat. No. 9,351,825, and a continuation-in-part of application No. 14/143,612, filed on Dec. 30, 2013, now abandoned, application No. 15/132,489, which is a continuation-in-part of application No. 14/712,827, filed on May 14, 2015, now abandoned, and a continuation of application No. 13/953,605, filed on Jul. 29, 2013, now Pat. No. 9,034,036, said application No. 14/712,827 is a continuation of application No. 13/472,354, filed on May 15, 2012, now Pat. No. 8,523,942, and a continuation of application No. 13/092,359, filed on Apr. 22, 2011, now Pat. No. 9,283,070, application No. 15/132,489, which is a continuation of application No. 14/741,230, filed on Jun. 16, 2015, now Pat. No. 9,358,101, which is a continuation of application No. 14/035,821, filed on Sep. 24, 2013, now Pat. No. 9,295,545, and a continuation-in-part of application No. 13/910,076, filed on Jun. 4, 2013, now Pat. No. 9,295,544, application No. 15/132,489, which is a continuation-in-part of application No. 14/968,518, filed on Dec. 14, 2015, which is a continuation of application No. 14/270,166, filed on May 5, 2014, now Pat. No. 9,211,186, and a continuation of application No. 13/155,327, filed on Jun. 7, 2011, now Pat. No. 8,764,823, application No. 15/132,489, which is a continuation-in-part of application No. 15/069,746, filed on Mar. 14, 2016, which is a continuation of application No. 13/092,359.

(60) Provisional application No. 61/398,098, filed on Jun. 21, 2010, provisional application No. 61/398,099, filed on Jun. 21, 2010, provisional application No. 61/398,107, filed on Jun. 21, 2010, provisional application No. 61/398,115, filed on Jun. 21, 2010, provisional application No. 61/519,098, filed on May 17, 2011, provisional application No. 61/921,782, filed on Dec. 30, 2013, provisional application No. 61/689,394, filed on Jun. 5, 2012.

(56) References Cited

U.S. PATENT DOCUMENTS

| | | |
|---|---|---|
| 4,118,808 A | 10/1978 | Poler |
| 4,122,556 A | 10/1978 | Poler |
| 4,159,546 A | 7/1979 | Shearing |
| 4,168,547 A | 9/1979 | Konstantinov et al. |
| 4,173,798 A | 11/1979 | Welsh |
| 4,174,543 A | 11/1979 | Kelman |
| 4,206,518 A | 6/1980 | Jardon et al. |
| 4,244,060 A | 1/1981 | Hoffer |
| 4,254,509 A | 3/1981 | Tennant |
| 4,277,851 A | 7/1981 | Choyce et al. |
| 4,298,995 A | 11/1981 | Poler |
| 4,304,012 A | 12/1981 | Richard |
| 4,409,690 A | 10/1983 | Gess |
| 4,409,691 A | 10/1983 | Levy |
| 4,424,597 A | 1/1984 | Schlegel |
| 4,441,217 A | 4/1984 | Cozean, Jr. |
| 4,477,931 A | 10/1984 | Kelman |
| 4,573,998 A | 3/1986 | Mazzocco |
| 4,585,457 A | 4/1986 | Kalb |
| 4,605,411 A | 8/1986 | Fedorov et al. |
| 4,629,462 A | 12/1986 | Feaster |
| 4,648,878 A | 3/1987 | Kelman |
| 4,664,665 A | 5/1987 | Reuss et al. |
| 4,664,666 A | 5/1987 | Barrett |
| 4,673,406 A | 6/1987 | Schlegel |
| 4,681,102 A | 7/1987 | Bartell |
| 4,704,123 A | 11/1987 | Smith |
| 4,710,195 A | 12/1987 | Giovinazzo |
| 4,718,904 A | 1/1988 | Thornton |
| 4,737,322 A | 4/1988 | Bruns et al. |
| 4,738,680 A | 4/1988 | Herman |
| 4,743,254 A | 5/1988 | Davenport |
| 4,753,655 A | 6/1988 | Hecht |
| 4,759,761 A | 7/1988 | Portnoy |
| 4,763,650 A | 8/1988 | Hauser |
| 4,765,329 A | 8/1988 | Cumming et al. |
| 4,769,033 A | 9/1988 | Nordan |
| 4,769,035 A | 9/1988 | Kelman |
| 4,772,283 A | 9/1988 | White |
| 4,778,463 A | 10/1988 | Hetland |
| 4,781,719 A | 11/1988 | Kelman |
| 4,790,847 A | 12/1988 | Woods |
| 4,793,344 A | 12/1988 | Cumming et al. |
| 4,813,955 A | 3/1989 | Achatz et al. |
| 4,816,030 A | 3/1989 | Robinson |
| 4,840,627 A | 6/1989 | Blumenthal |
| 4,842,599 A | 6/1989 | Bronstein |
| 4,842,601 A | 6/1989 | Smith |
| 4,846,833 A | 7/1989 | Cumming |
| 4,862,885 A | 9/1989 | Cumming |
| 4,865,601 A | 9/1989 | Caldwell et al. |
| 4,868,251 A | 9/1989 | Reich et al. |
| 4,880,427 A | 11/1989 | Anis |
| 4,888,012 A | 12/1989 | Horn et al. |
| 4,892,543 A | 1/1990 | Turley |
| 4,919,130 A | 4/1990 | Stoy et al. |
| 4,932,966 A | 6/1990 | Christie et al. |
| 4,932,968 A | 6/1990 | Caldwell et al. |
| 4,932,970 A | 6/1990 | Portney |
| 4,936,850 A | 6/1990 | Barrett |
| 4,963,148 A | 10/1990 | Sulc et al. |
| 4,969,897 A | 11/1990 | Kalb |
| 4,976,716 A | 12/1990 | Cumming |
| 4,978,354 A | 12/1990 | Van Gent |
| 4,994,082 A | 2/1991 | Richards et al. |
| 5,047,051 A | 9/1991 | Cumming |
| 5,066,297 A | 11/1991 | Cumming |
| 5,078,742 A | 1/1992 | Dahan |
| 5,089,022 A | 2/1992 | Koester et al. |
| 5,139,518 A | 8/1992 | White |
| 5,141,507 A | 8/1992 | Paraekh |
| 5,152,788 A | 10/1992 | Isaacson et al. |
| 5,152,789 A | 10/1992 | Willis |
| 5,171,319 A | 12/1992 | Keates et al. |
| 5,171,320 A | 12/1992 | Nishi |
| 5,180,390 A | 1/1993 | Drews |
| 5,217,490 A | 6/1993 | Sayano et al. |
| 5,275,604 A | 1/1994 | Rheinish et al. |
| 5,275,623 A | 1/1994 | Sarfarazi |
| 5,275,624 A | 1/1994 | Hara et al. |
| 5,290,310 A | 3/1994 | Makower et al. |
| 5,304,182 A | 4/1994 | Rheinish et al. |
| 5,324,306 A | 6/1994 | Makower et al. |
| 5,326,347 A | 7/1994 | Cumming |
| 5,366,502 A | 11/1994 | Patel |
| 5,376,115 A | 12/1994 | Jansen |
| 5,425,734 A | 6/1995 | Blake |
| 5,443,506 A | 8/1995 | Garabet |
| 5,474,562 A | 12/1995 | Orchowski et al. |
| 5,476,514 A | 12/1995 | Cumming |
| 5,489,302 A | 2/1996 | Skottun |
| 5,496,366 A | 3/1996 | Cumming |
| 5,522,891 A | 6/1996 | Klaas |
| 5,562,731 A | 10/1996 | Cumming |
| 5,578,042 A | 11/1996 | Cumming |
| 5,578,078 A | 11/1996 | Nakajima et al. |
| 5,607,472 A | 3/1997 | Thompson |
| 5,611,968 A | 3/1997 | Grisoni et al. |
| 5,647,865 A | 7/1997 | Swinger |
| 5,674,282 A | 10/1997 | Cumming |
| 5,686,414 A | 11/1997 | Scannon |
| 5,699,142 A | 12/1997 | Lee et al. |
| 5,716,403 A | 2/1998 | Tran et al. |
| 5,800,532 A | 9/1998 | Lieberman |

(56) References Cited

U.S. PATENT DOCUMENTS

| | | |
|---|---|---|
| 5,837,156 A | 11/1998 | Cumming |
| 5,843,187 A | 12/1998 | Bayers |
| 5,873,879 A | 2/1999 | Figueroa et al. |
| 5,919,230 A | 7/1999 | Sambursky |
| 5,944,725 A | 8/1999 | Cicenas et al. |
| 5,968,094 A | 10/1999 | Werblin et al. |
| 5,984,914 A | 11/1999 | Cumming |
| 6,007,579 A | 12/1999 | Lipshitz et al. |
| 6,013,101 A | 1/2000 | Israel |
| 6,015,435 A | 1/2000 | Valunin et al. |
| 6,027,531 A | 2/2000 | Tassignon |
| 6,051,024 A | 4/2000 | Cumming |
| 6,066,171 A | 5/2000 | Lipshitz et al. |
| 6,066,172 A | 5/2000 | Huo et al. |
| 6,113,633 A | 9/2000 | Portney |
| 6,129,760 A | 10/2000 | Fedorov et al. |
| 6,161,544 A | 12/2000 | DeVore |
| 6,164,282 A | 12/2000 | Gwon et al. |
| 6,176,878 B1 | 1/2001 | Gwon et al. |
| 6,179,870 B1 | 1/2001 | Sourdille et al. |
| 6,193,750 B1 | 2/2001 | Cumming |
| 6,197,058 B1 | 3/2001 | Portney |
| 6,197,059 B1 | 3/2001 | Cumming |
| 6,217,612 B1 | 4/2001 | Woods |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,387,126 B1 | 5/2002 | Cumming |
| 6,391,056 B2 | 5/2002 | Cumming |
| 6,406,494 B1 | 6/2002 | Laguette et al. |
| 6,409,763 B1 | 6/2002 | Brady |
| 6,413,276 B1 | 7/2002 | Werblin |
| 6,419,697 B1 | 7/2002 | Kelman |
| 6,423,094 B1 | 7/2002 | Sarfarazi |
| 6,443,985 B1 | 9/2002 | Woods |
| 6,451,056 B1 | 9/2002 | Cumming |
| 6,461,384 B1 | 10/2002 | Hoffmann et al. |
| 6,488,708 B2 | 12/2002 | Sarfarazi |
| 6,494,911 B2 | 12/2002 | Cumming |
| 6,497,708 B1 | 12/2002 | Cumming |
| 6,503,275 B1 | 1/2003 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,540,353 B1 | 4/2003 | Dunn |
| 6,558,420 B2 | 5/2003 | Green |
| 6,613,343 B2 | 9/2003 | Dillingham et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,660,035 B1 | 12/2003 | Lang et al. |
| 6,660,036 B2 | 12/2003 | Cumming |
| 6,685,741 B2 | 2/2004 | Landreville et al. |
| 6,695,881 B2 | 2/2004 | Peng et al. |
| 6,749,634 B2 | 6/2004 | Hanna |
| 6,767,363 B1 | 7/2004 | Bandhauer et al. |
| 6,849,091 B1 | 2/2005 | Cumming |
| 6,858,040 B2 | 2/2005 | Nguyen et al. |
| 6,881,225 B2 | 4/2005 | Okada |
| 6,884,263 B2 | 4/2005 | Valyunin |
| 6,921,416 B2 | 7/2005 | Khoury |
| 6,926,736 B2 | 8/2005 | Peng |
| 6,932,839 B1 | 8/2005 | Kamerling et al. |
| 6,969,403 B2 | 11/2005 | Peng |
| 6,972,033 B2 | 12/2005 | McNicholas |
| 7,018,409 B2 | 3/2006 | Glick |
| 7,025,783 B2 | 4/2006 | Brady |
| 7,037,338 B2 | 5/2006 | Nagamoto |
| 7,048,760 B2 | 5/2006 | Cumming |
| 7,097,660 B2 | 8/2006 | Portney |
| 7,125,422 B2 | 10/2006 | Woods et al. |
| 7,150,759 B2 | 12/2006 | Paul et al. |
| 7,150,760 B2 | 12/2006 | Zhang |
| 7,229,475 B2 | 6/2007 | Glazier |
| 7,229,476 B2 | 6/2007 | Azar |
| 7,300,464 B2 | 11/2007 | Tran |
| 7,326,246 B2 | 2/2008 | Brady |
| 7,341,599 B1 | 3/2008 | Peyman |
| 7,435,258 B2 | 10/2008 | Blake |
| 7,435,259 B2 | 10/2008 | Cumming |
| 7,553,327 B2 | 6/2009 | Cumming |
| 7,662,180 B2 | 2/2010 | Paul et al. |
| 7,763,070 B2 | 7/2010 | Cumming |
| 7,837,730 B2 | 11/2010 | Cumming |
| 7,981,155 B2 | 7/2011 | Cumming |
| 7,985,253 B2 | 7/2011 | Cumming |
| 8,038,711 B2 | 10/2011 | Clarke |
| 8,080,056 B2 | 12/2011 | Cumming |
| 8,100,965 B2 | 1/2012 | Cumming et al. |
| 8,109,998 B2 | 2/2012 | Cumming |
| 8,163,015 B2 | 4/2012 | Cumming |
| 8,216,308 B2 | 7/2012 | Blake et al. |
| 8,388,608 B1 | 3/2013 | Kaluzna |
| 8,523,942 B2 | 9/2013 | Cumming |
| 8,734,512 B2 | 5/2014 | Cumming |
| 8,764,823 B2 | 7/2014 | Cumming |
| 9,034,036 B2 | 5/2015 | Cumming |
| 9,211,186 B2 | 12/2015 | Cumming |
| 2001/0001836 A1 | 5/2001 | Cumming |
| 2002/0120329 A1 | 8/2002 | Lang et al. |
| 2002/0138140 A1 | 9/2002 | Hanna |
| 2003/0060881 A1 | 3/2003 | Glick et al. |
| 2003/0078658 A1 | 4/2003 | Zadno-Azizi |
| 2003/0097177 A1 | 5/2003 | Tran |
| 2003/0109925 A1 | 6/2003 | Ghazizadeh et al. |
| 2003/0135272 A1 | 7/2003 | Brady et al. |
| 2003/0142269 A1 | 7/2003 | Cumming |
| 2003/0171808 A1 | 9/2003 | Phillips |
| 2003/0171809 A1 | 9/2003 | Phillips |
| 2003/0187505 A1 | 10/2003 | Liao |
| 2003/0199977 A1 | 10/2003 | Cumming |
| 2003/0204257 A1 | 10/2003 | Southard |
| 2004/0002757 A1 | 1/2004 | Lai et al. |
| 2004/0015236 A1 | 1/2004 | Sarfarazi |
| 2004/0082993 A1 | 4/2004 | Woods |
| 2004/0082994 A1 | 4/2004 | Woods et al. |
| 2004/0111152 A1 | 6/2004 | Kelman |
| 2004/0148023 A1 | 7/2004 | Shu |
| 2004/0215207 A1 | 10/2004 | Cumming |
| 2004/0215340 A1 | 10/2004 | Messner et al. |
| 2004/0220666 A1 | 11/2004 | Cumming |
| 2004/0243232 A1 | 12/2004 | Cumming |
| 2004/0249456 A1 | 12/2004 | Cumming |
| 2005/0021140 A1 | 1/2005 | Liao |
| 2005/0027354 A1 | 2/2005 | Brady et al. |
| 2005/0075732 A1 | 4/2005 | Israel |
| 2005/0096741 A1 | 5/2005 | Cumming |
| 2005/0107875 A1 | 5/2005 | Cumming |
| 2005/0125058 A1 | 6/2005 | Cumming et al. |
| 2005/0137703 A1 | 6/2005 | Chen |
| 2005/0267576 A1 | 12/2005 | Cumming |
| 2005/0288784 A1 | 12/2005 | Peyman |
| 2006/0064077 A1 | 3/2006 | Peyman |
| 2006/0064162 A1 | 3/2006 | Klima |
| 2006/0100704 A1 | 5/2006 | Blake et al. |
| 2006/0111776 A1 | 5/2006 | Glick et al. |
| 2006/0116764 A1 | 6/2006 | Simpson |
| 2006/0149369 A1 | 7/2006 | Cumming et al. |
| 2007/0021832 A1 | 1/2007 | Nordan |
| 2007/0032867 A1 | 2/2007 | Cumming |
| 2007/0129800 A1 | 6/2007 | Cumming |
| 2007/0129803 A1 | 6/2007 | Cumming et al. |
| 2007/0135915 A1 | 6/2007 | Klima |
| 2007/0142908 A1 | 6/2007 | Xu |
| 2007/0198084 A1 | 8/2007 | Cumming et al. |
| 2007/0244472 A1 | 10/2007 | Kuhn et al. |
| 2008/0027538 A1 | 1/2008 | Cumming |
| 2008/0027539 A1 | 1/2008 | Cumming |
| 2008/0027540 A1 | 1/2008 | Cumming |
| 2008/0046077 A1 | 2/2008 | Cumming |
| 2008/0086208 A1 | 4/2008 | Nordan |

(56) References Cited

U.S. PATENT DOCUMENTS

| | | |
|---|---|---|
| 2008/0154362 A1 | 6/2008 | Cumming |
| 2008/0281415 A1 | 11/2008 | Cumming |
| 2008/0281416 A1 | 11/2008 | Cumming |
| 2008/0288066 A1 | 11/2008 | Cumming |
| 2008/0294254 A1 | 11/2008 | Cumming et al. |
| 2008/0319545 A1 | 12/2008 | Cumming |
| 2009/0005866 A1 | 1/2009 | Cumming |
| 2009/0234449 A1 | 9/2009 | De Juan, Jr. et al. |
| 2009/0248154 A1 | 10/2009 | Dell |
| 2010/0004742 A1 | 1/2010 | Cumming |
| 2010/0057202 A1 | 3/2010 | Bogaert |
| 2011/0313519 A1 | 12/2011 | Cumming |
| 2011/0313524 A1 | 12/2011 | Cumming |
| 2011/0313525 A1 | 12/2011 | Cumming |
| 2011/0313526 A1 | 12/2011 | Cumming |
| 2012/0296424 A1 | 11/2012 | Betser |
| 2012/0310344 A1 | 12/2012 | Cumming |
| 2013/0073039 A1 | 3/2013 | Mirlay |
| 2013/0231742 A1 | 9/2013 | Deacon et al. |
| 2014/0088699 A1 | 3/2014 | Cumming |
| 2014/0094909 A1 | 4/2014 | Cumming |
| 2014/0155871 A1 | 6/2014 | Cumming |
| 2014/0172093 A1 | 6/2014 | Cumming |
| 2015/0012088 A1 | 1/2015 | Cumming |
| 2015/0073550 A1 | 3/2015 | Cumming |
| 2015/0088254 A1 | 3/2015 | Cumming |
| 2015/0182328 A1 | 7/2015 | Cumming |
| 2015/0245904 A1 | 9/2015 | Cumming |
| 2015/0245905 A1 | 9/2015 | Cumming |
| 2015/0272726 A1 | 10/2015 | Cumming |

FOREIGN PATENT DOCUMENTS

| | | |
|---|---|---|
| DE | 3626869 | 2/1988 |
| FR | 2728458 | 6/1996 |
| FR | 2728459 | 6/1996 |
| FR | 2734472 | 11/1996 |
| FR | 2765797 | 1/1999 |
| FR | 2991572 | 12/2013 |
| GB | 2171912 | 9/1986 |
| GB | 2226246 | 6/1990 |
| JP | 2003-190193 | 7/2003 |
| SU | 1123685 | 11/1984 |
| WO | WO 93/05733 | 4/1993 |
| WO | WO 01/19288 | 3/2001 |
| WO | WO 01/19289 | 3/2001 |
| WO | WO 03/017873 | 3/2003 |
| WO | WO 2007/037180 | 4/2007 |
| WO | WO 2009/048656 | 4/2009 |
| WO | WO 2009/086511 | 7/2009 |
| WO | WO 2011/151839 | 12/2011 |

OTHER PUBLICATIONS

Internet Archive Wayback Machine; Crystalens—Is Crystalens right for you?; downloaded from http://web.archive.org/web/20141025080709/http://crystalens.com/en-us/iscrystalensrightforyou.aspx (Archived Oct. 25, 2014; printed on Aug. 12, 2015).

Dykstra, M., et al. Biological Electron Microscopy: Theory, Techniques, and Troublshooting, 2003, p. 81.

International Search Report and Written Opinion for PCT/US13/61452 dated Feb. 24, 2014 in 11 pages.

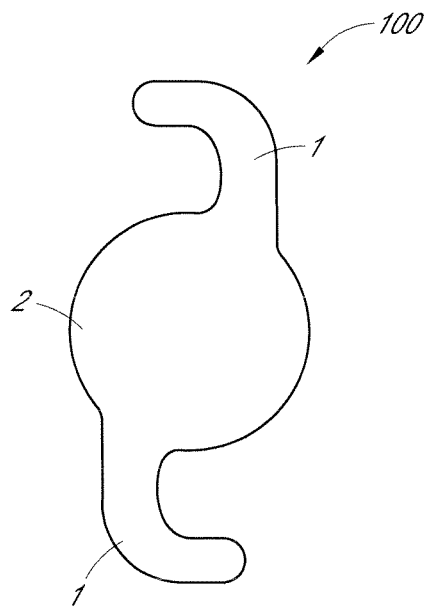
FIG. 1
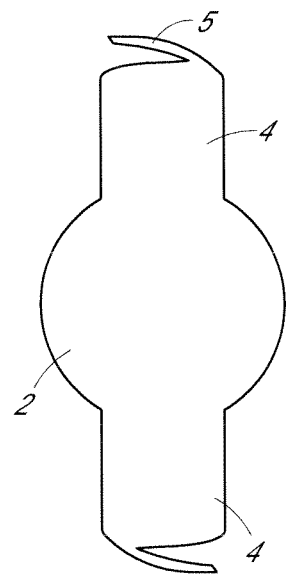
FIG. 2
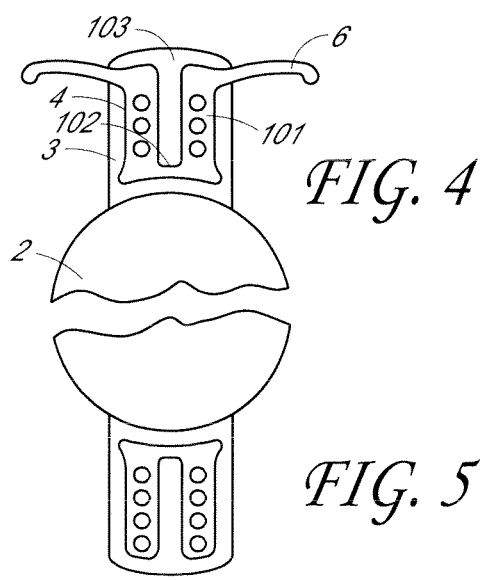
FIG. 4
FIG. 5
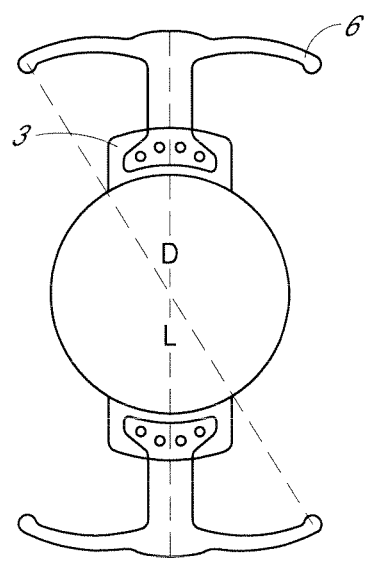
FIG. 3

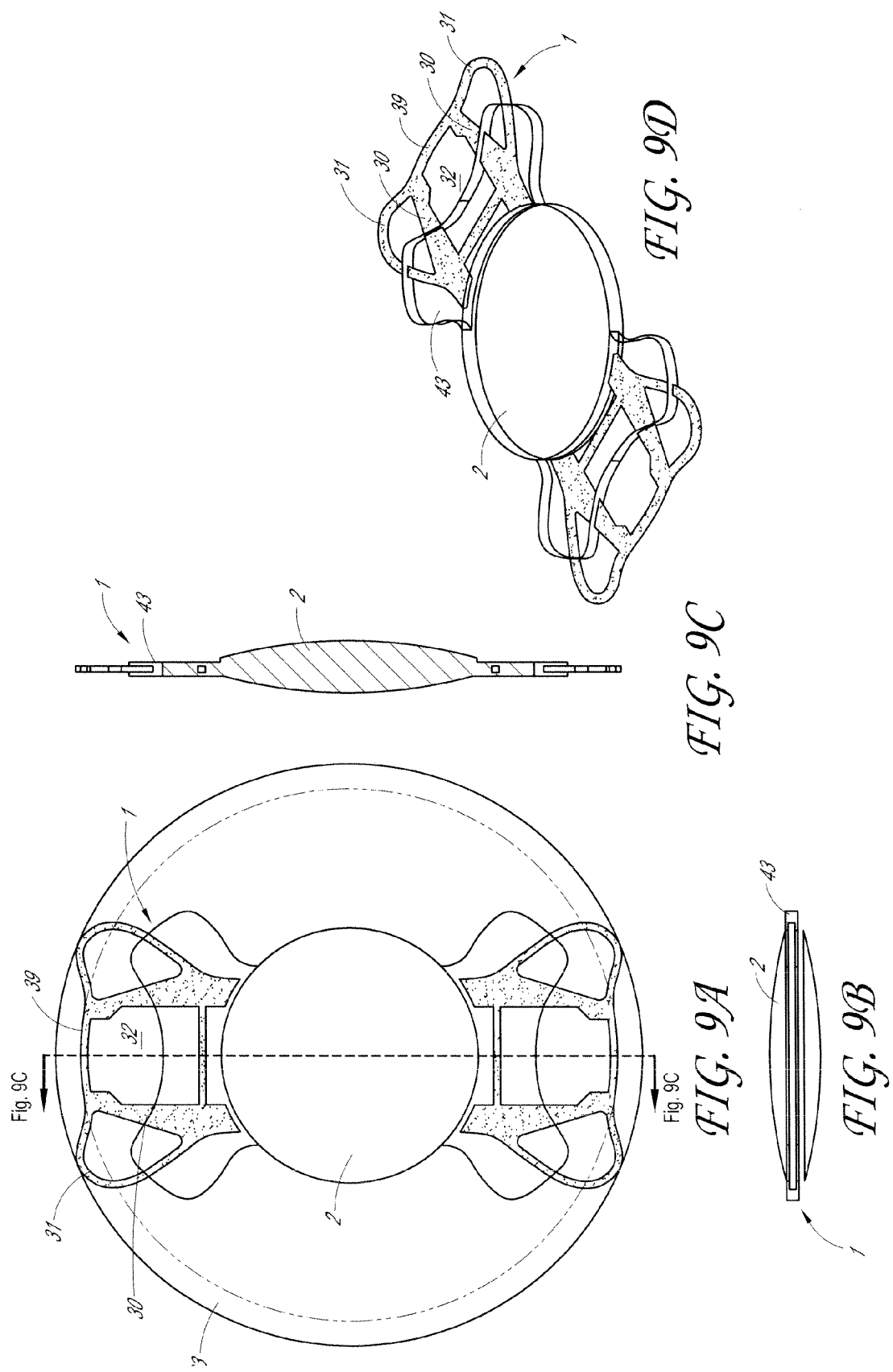

FOLDABLE INTRAOCULAR LENS WITH RIGID HAPTICS

CROSS-REFERENCE TO RELATED APPLICATIONS

This application is a continuation of U.S. patent application Ser. No. 14/143,612, filed on Dec. 30, 2013, currently, the contents of which are hereby incorporated by reference herein in their entireties.

This application is also a continuation-in-part of U.S. patent application Ser. No. 13/017,189, filed on Jan. 31, 2011, currently, which claims priority to U.S. Provisional Application Nos. 61/398,098, filed on Jun. 21, 2010, 61/398,099, filed on Jun. 21, 2010, 61/398,107, filed on Jun. 21, 2010 and 61/398,115, filed on Jun. 21, 2010, the contents of which are hereby incorporated by reference herein in their entireties.

This application is also a continuation-in-part of U.S. patent application Ser. No. 14/257,933, filed on Apr. 21, 2014, currently, which is a continuation-in-part of U.S. patent application Ser. No. 14/143,612, filed on Dec. 30, 2013, currently, the contents of which are hereby incorporated by reference herein in their entireties.

This application is also a continuation-in-part of U.S. patent application Ser. No. 14/274,352, filed on May 9, 2014, currently, which is a continuation of U.S. patent application Ser. No. 13/472,893, filed on May 16, 2012, now U.S. Pat. No. 8,734,512, which also claims priority to U.S. Provisional Application No. 61/519,098, filed on May 17, 2011, the contents of which are hereby incorporated by reference herein in their entireties.

This application is also a continuation-in-part of U.S. patent application Ser. No. 14/541,188, filed on Dec. 29, 2014, currently, which is a continuation-in-part of U.S. patent application Ser. No. 14/257,933, filed on Apr. 21, 2014, currently, which is a continuation-in-part of U.S. patent application Ser. No. 14/143,612, filed on Dec. 30, 2013, currently, which also claims priority to U.S. Provisional Application No. 61/921,782, filed on Dec. 30, 2013, the contents of which are hereby incorporated by reference herein in their entireties.

This application is also a continuation-in-part of U.S. patent application Ser. No. 14/712,827, filed on May 14, 2015, currently, which is a continuation of U.S. patent application Ser. No. 13/953,605, filed on Jul. 29, 2013, now U.S. Pat. No. 9,034,036, which is a continuation of U.S. patent application Ser. No. 13/472,354, filed on May 15, 2012, now U.S. Pat. No. 8,523,942, which is a continuation of U.S. patent application Ser. No. 13/092,359, filed on Apr. 22, 2011, now U.S. Pat. No. 9,283,070, the contents of which are hereby incorporated by reference herein in their entireties.

This application is also a continuation-in-part of U.S. patent application Ser. No. 14/741,230, filed on Jun. 16, 2015, currently, which is a continuation of U.S. patent application Ser. No. 14/035,821, filed on Sep. 24, 2013, now U.S. Pat. No. 9,295,545, which is a continuation-in-part of U.S. patent application Ser. No. 13/910,076, filed on Jun. 4, 2013, now U.S. Pat. No. 9,295,544, which also claims priority to U.S. Provisional Application No. 61,689,394, filed on Jun. 5, 2012, the contents of which are hereby incorporated by reference herein in their entireties.

This application is also a continuation-in-part of U.S. patent application Ser. No. 14/968,518, filed on Dec. 14, 2015, currently, which is a continuation of U.S. patent application Ser. No. 14/270,166, filed on May 5, 2014, now U.S. Pat. No. 9,211,186, which is a continuation of U.S. patent application Ser. No. 13/155,327, filed on Jun. 7, 2011, now U.S. Pat. No. 8,764,823, which also claims priority to U.S. Provisional Application Nos. 61/398,098, filed on Jun. 21, 2010, 61/398,099, filed on Jun. 21, 2010, 61/398,107, filed on Jun. 21, 2010 and 61/398,115, filed on Jun. 21, 2010, the contents of which are hereby incorporated by reference herein in their entireties.

This application is also a continuation-in-part of U.S. patent application Ser. No. 15/069,746, filed on Mar. 14, 2016, currently, which is a continuation of U.S. patent application Ser. No. 13/092,359, filed on Apr. 22, 2011, now U.S. Pat. No. 9,283,070, which also claims priority to U.S. Provisional Application Nos. 61/398,098, filed on Jun. 21, 2010, 61/398,099, filed on Jun. 21, 2010, 61/398,107, filed on Jun. 21, 2010 and 61/398,115, filed on Jun. 21, 2010, the contents of which are hereby incorporated by reference herein in their entireties.

BACKGROUND

The present disclosure relates to an intraocular lenses with haptics that are more longitudinally rigid than the optic.

DESCRIPTION OF THE RELATED ART

Surgical procedures for treating cataracts that are commonly employed today involve implanting an intraocular lens (IOL) into the eye. In such procedures, a normal human lens that has been clouded over by a cataract is typically replacing by the IOL.

Many breakthrough changes in cataract surgery during the last forty years have yielded a reliable surgical procedure that regularly produces favorable patient outcomes. Modern surgical techniques also have made the operation very safe when performed by a competent surgeon.

The procedure can now also be considered a surgical means of treating myopia, hyperopia or astigmatism, as IOLs with the appropriate power to provide optical correction can be inserted in the eye.

One of the remaining problems to be solved though is to make the post-operative uncorrected distant visions (e.g., without eyeglasses or contacts) more accurate than they now are. This would then make lens surgery comparable to corneal surgery so far as the uncorrected vision is concerned, making common surgical cataract surgery or removal of a clear lens, a refractive procedure.

SUMMARY OF THE INVENTION

Various embodiments described here comprise intraocular lens structures that more accurately places the optic of an intraocular lens in a more consistently repeatable and predictable location along the optical or visual axis of the eye in comparison to other lens designs, thereby making post-operative uncorrected vision (e.g., without the aid of eyeglasses or contacts) more predictable.

This disclosure, for example, describes an intraocular lens comprising rigid haptics connected to a foldable optic. Connecting the foldable optic to rigid haptics prevents deformation of the haptics when subjected to the action of the ciliary muscle and fibrosis after implantation into the empty capsular bag during cataract surgery. Two rigid haptics of substantially equal length generally leave the lens optic in the same position along the optical or visual axis of the eye as it was when it was placed into the capsular bag at the time of surgery. The lens may be designed to be slightly longer than the capsular bag or shorter, and may be uniplanar, curved or angulated, having in some embodiments a fixed angle at the time of manufacture of between 5 to 40 degrees that will vault the lens optic forward or backwards upon insertion into the capsular bag.

Accordingly, various embodiments are directed toward a non-accommodating intraocular lens having at least one rigid haptic connected to a flexible optic. The rigid structure is rigid longitudinally. A longitudinal length of the intraocular lens may be fixed prior to insertion into the eye. The at least one haptic can be directly connected to the optic as a lens manufactured as a single piece, or indirectly connected to the optic by a short extension of the optic.

The longitudinally rigid haptic can comprise the same material as the flexible optic and be manufactured as one piece, the haptic made rigid by increasing its thickness and or its width. The rigid haptic may be made rigid by having a rigid structure; a chassis, partially or completely embedded into the flexible material of the optic such as silicone or acrylic. The rigid material of the chassis is designed to make the haptic rigid and to fixate the lens within the capsular bag of the eye. Fixation can be done using flexible loops (open or closed loops) contiguous with the internal chassis extending tangentially from the distal lateral aspects of the chassis, or by creating open spaces within the confines of the diameter of the optic, or by closed loops extending beyond the diameter of the optic. The loops may be made rigid or compressible.

In any of the above-mentioned intraocular lens aspects, the rigid structure can include at least one longitudinally extending strut. In certain aspects, the rigid structure can include a closed structure at least partially surrounding the at least one longitudinally extending strut to form at least one open area (e.g., one, two, or three open areas). In certain aspects, the loop structure can include a first width and a second width. The first width can be closer to a distal end of the loop structure, and the first width can be greater than the second width. In certain aspects, the loop structure can have a width that is less than the width of the at least one longitudinally extending strut. For example, the width of the loop structure can be less than about 25% and/or greater than about 5% of the widths of the at least one longitudinally extending strut (e.g., less than 20%, less than 15%, or less than 10%).

The rigid haptics may have T shaped flexible fingers at the distal end of the otherwise rigid haptic.

In certain variants, the rigid structure can be a plate haptic. The plate haptic can include a thin bar disposed at either the distal or proximal end of the haptic. Further, the plate haptic can include an open area proximal to the thin bar.

In any of the above mentioned intraocular lens aspects, the optic can be uniplanar or biased posteriorly or anteriorly at the time of manufacture, prior to insertion into an eye. The structures also can have a fixed length that can resist deformation by the action of the ciliary muscle and fibrosis.

Accordingly, various embodiments disclosed herein may comprise an intraocular lens comprising flexible optic and at least one haptic connected to the optic. The at least one haptic comprises a rigid structure. The intraocular lens comprises a non-accommodating IOL having a longitudinal length that is fixed.

Various embodiments comprise an intraocular lens comprising flexible optic and at least one haptic connected to the optic wherein the rigid haptic is more rigid than the flexible optic. The intraocular lens comprises a non-accommodating IOL.

Various embodiments comprise an intraocular lens where the flexible optic may connect to a haptic of the same material and the haptic is made rigid by being widening or thickening its structure or by a combination of both.

A wide variety of variations are possible. For example, any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein.

BRIEF DESCRIPTION OF THE FIGURES

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIG. 1 illustrates a non-accommodating lens with loops (e.g. open loops) that comprises an optic and haptics in one piece comprising one material, for example acrylic.

FIG. 2 illustrates a plate haptic non-accommodating intraocular lens (NAIL) with small fixation loops all made of one piece.

FIG. 3 illustrates an embodiment of a haptic having a single rigid longitudinal structure with T shaped flexible distal lateral extensions.

FIG. 4 illustrates a non-accommodating intraocular lens (NAIL) having a chassis embedded into the same flexible material as the optic.

FIG. 5 is the same as FIG. 4 but without the fixation loops.

FIG. 9A illustrates a rigid haptic intraocular lens having a triple loop structure, the three loops (e.g. closed loops) being partially covered with the same flexible material as the optic.

FIG. 9B is a top view of the intraocular lens shown in FIG. 9A.

FIG. 9C is a cross-sectional view of the intraocular lens shown in FIG. 9A.

FIG. 9D is a perspective view of the intraocular lens shown in FIG. 9A.

DETAILED DESCRIPTION OF THE PREFERRED EMBODIMENTS

Figure 6:
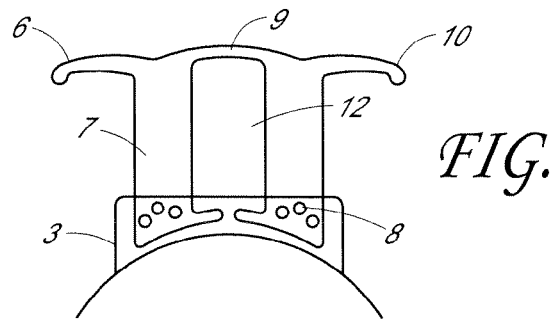
FIG. 6 illustrates another NAIL having two exposed rigid longitudinal plates or struts connected by a thin transverse bar creating an enclosed open space and fixation loops (e.g. open loops) to facilitate fixation of the lens into the capsular bag.

Many intraocular lenses have an optic connected to two or more flexible haptics, which function to center and fixate the lens in the empty capsular bag of the human lens. These haptics can be formed by two flexible loops.

The circular ciliary muscle inside the eye, part of the autonomic nervous system and active throughout life, is responsible for changing the focus of the eye. When the patient implanted with standard loop intraocular lenses attempts to see during the early post-operative period subsequent to cataract surgery, the ciliary muscle, still active, applies end-to-end pressure (e.g., in the longitudinal direction of the lens) that impinges on the flexible loops moving them forwards and backwards, centrally and peripherally within the capsular bag. This movement can shift the location of the lens in the capsular bag. Also during this time, fibrosis is taking place and the loops do not necessarily end up fixed in the cul-de-sac of the bag where they were placed at the time of surgery. Instead, the loops may be, for example, stuck somewhere between the cul-de-sac of the capsular bag and the optic. Changing the location of the haptic loops within the bag can also change the position of the lens optic along the axis of the eye and cause decentration and tilting of the optic. The lens position is thus not where it was calculated and anticipated to be. Consequently, the uncorrected distance vision (e.g. without glasses or contact lenses) and post-operative refractions are not what was expected prior to surgery. In some cases, the loops of a lens have been compressed centrally to lie in front or behind, the lens optic.

Various embodiments disclosed herein, however, can address this problem. See, for example, the intraocular implants illustrated in FIGS. 1-4. The intraocular implants comprise an optic 2 and opposing rigid haptics 1 with flexible loop lateral extensions (e.g. open loops). In FIGS. 4 through 8 only one of the two haptics, however, is shown in these figures. The haptics 1 can be connected to the optic 2 either directly (see FIGS. 1 and 2) or to a short thick rigid extension 3 of the optic 2 (see FIGS. 3 to 8). The short extension 3 can be constructed from the same material as the optic 2. Further, the short rigid extension 3 can be integrally molded with the optic 2 or separately formed from the optic 2. To facilitate connection, holes are made through the rigid component of the haptic through which the flexible component can fuse during the manufacturing process (see FIGS. 6-8). The short thick rigid extension 3 may be desirable to facilitate the connection between the optic 2 and the haptic 1 without encroaching on the circumference of the optic 2.

The optic 2 may comprise substantially transparent biocompatible flexible optical material, e.g. acrylic, hydrogel, or silicone, and may be biconvex, plano convex, concave/plano, toric, aspheric, spherical Fresnel multifocal or any combination. The optic and may be used in combination with a second optic within the eye.

The haptics 1 can be designed to be rigid and resistant to deformation from the action of the ciliary muscle. In particular, the haptics may resist pressure imposed in the longitudinal direction by the ciliary muscle and fibrosis without flexing. Unlike flexible haptics that are traditionally used with non-accommodating and accommodating lenses, the rigid haptics 1 better facilitate centration and provide a more consistent location of the optic along the axis of the eye because the rigid haptics 1 are resistant to compression.

As illustrated in FIG. 1, in some embodiments, the haptics 1 can include an open loop. Some haptics 1 can include one or more closed loops. (See also FIGS. 6 to 9 discussed more fully below).

FIG. 1 shows a lens manufactured for example from acrylic as one piece, with the optic contiguous with the curved open loop like rigid haptic. As with all these lens designs the lens may be uniplanar or the optic may be vaulted backwards or forwards at the time of surgery.

FIG. 2 shows a lens manufactured of one material with a rigid plate-like haptic structure 4 and small distal fixation fingers 5.

FIG. 3 schematically illustrates an embodiment of a haptic having a single rigid longitudinal structure with T shaped flexible distal lateral extensions, the rigid longitudinal structure attached to a short thickened extension 3 of the optic.

FIGS. 4 and 5 show two rigid struts/plates attached to a short thickened extension of the optic 3 with a proximal transverse connecting bar 1 or 2 between the two struts/plates. The chassis which is embedded into the flexible material 103 has external distal fixation fingers 6 in FIG. 4.

FIG. 6 illustrates two rigid struts/plates 7, with finger like extensions 6, with knob like peripheral ends 10, embedded proximally into a thick rigid extension 3 of the optic 2, anchored to it by fusion of the flexible material through holes 8, during the manufacturing process. The two plates connected distally by a thin transverse crossbar 9.

Figure 7:
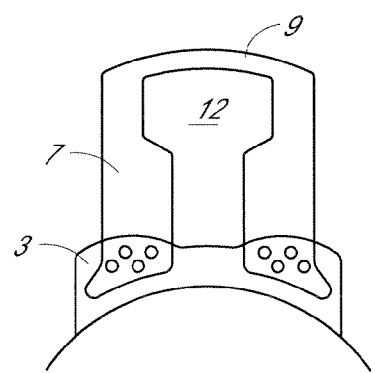
FIG. 7 is the same as FIG. 6 without the fixation loops.

FIG. 7 is similar to FIG. 6 except that fixation into the capsular bag is achieved without the flexible fingers by fusion of the anterior and posterior capsules over the distal thin connecting bar to fibrose through the open space 12 enclosed by the struts/plates 7, bar 9 and thick rigid extension 3. The width of each strut would be between 1.0 and 3.0 mm so that the lens can be folded longitudinally to be compressed to be inserted through an incision of 3.0 mm or less.

Figure 8:
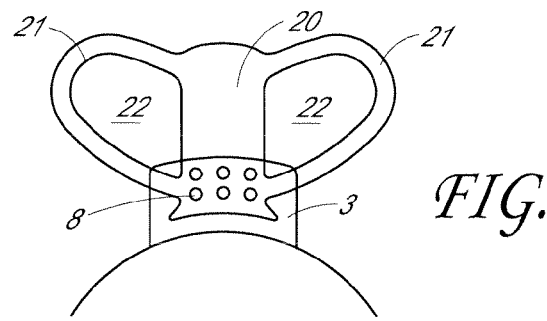
FIG. 8 illustrates another embodiment of a haptic having a rigid haptic double loop structure.

FIG. 8 comprises a single plate 20 to which are attached on each of its lateral sides two rigid closed loops 21 to provide two enclosed spaces 22 or opening into which the capsular bag can fibrose to fix the lens haptics within the capsular bag.

FIGS. 9A-9D illustrate a non-accommodating IOL comprising a flexible optic 2 with rigid haptics 1, comprising a chassis with two longitudinal rigid struts/plates 30 from which extend two laterally extending closed loops 31, designed to both fixate and center the lens within the capsular bag. A distal bar 39 extends between the two struts/plates 30 creating a central enclosed open region 32. The chassis is partially embedded proximally within the flexible material 43 of the optic. The cul-de-sac of the capsular bag 33 is shown partially distended to a radius of 11.5 mm.

Figure 10:
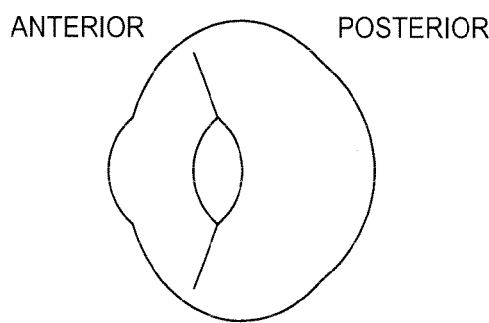
FIG. 10 illustrates a side view of an intraocular lens with the optic vaulted posteriorly at the time of manufacture
Figure 11:
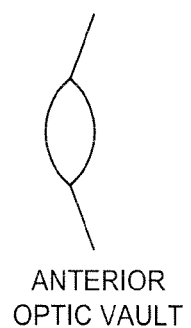
FIG. 11 illustrates a side view of an intraocular lens vaulted anteriorly at the time of manufacture.
Figure 12:
FIG. 12 illustrates a side view of an intraocular lens having haptics disposed in a common plane.

FIGS. 10, 11, and 12 show the possible side elevations of the lens, which can be vaulted posteriorly (FIG. 10), anteriorly (FIG. 11) and uniplanar (FIG. 12).

Figure 13:
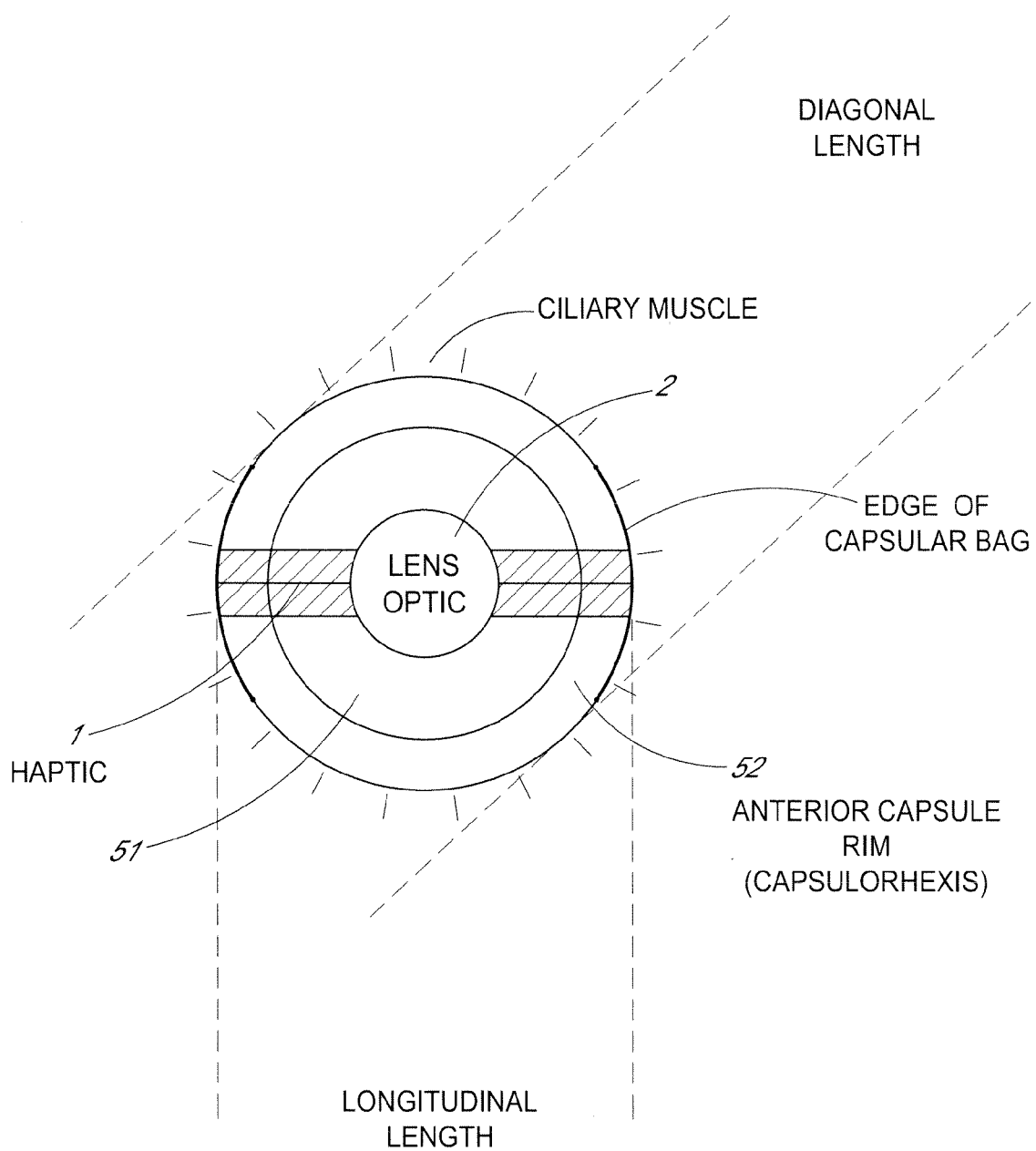
FIG. 13 illustrates a schematic diagram of an intraocular lens implanted in a capsular bag.

FIG. 13 shows a schematic of the non-accommodating intraocular lens within the capsular bag. Visible are the anterior capsule rim 30, the posterior capsule 31 and the anterior capsule rim 32 inside of which is the bag cul-de-sac.

The lenses are designed to have a flexible optic connected to rigid haptics that are rigid longitudinally but flexible transversely, so that the lens can be compressed into an insertion device to be inserted into the eye through an incision of 3.0 mm or less. The haptics are rigid enough to prevent flexion in the longitudinal direction when subjected to the pressure exerted on them by action of the ciliary muscle and by fibrosis. The thin transverse connecting bars of the chassis are flexible to enable the lenses to be folded and compressed about the longitudinal axis.

In various embodiments, the overall length D of the lens 10 may be from about 9.5 mm to about 14.0 mm as measured diagonally across the lens and optic 2 from the tips of the fixation lateral loops 10 on opposite sides of the lens. See e.g. FIGS. 3 and 13. The diagonal distance extends through the center of the optic. The longitudinal length L of the lens 100 (also shown in FIGS. 3 and 13) can be at least the diameter of the average capsular bag. For example, the longitudinal length of the lens 10 can be from about 9.5 mm to about 12.0 mm, the preferred length being about 10.5 mm in various embodiments, which is slightly longer than the average capsular bag diameter, in certain embodiments.

The haptic component extending from the flexible optic is made rigid in some embodiments by its small length, less than 1 mm, and a thickness more than 1 mm and may comprise at least in part acrylic, silicone or other inert flexible material, and the rigid component, polyimide, acrylic or other rigid materials. The haptic may be made rigid longitudinally provided in some embodiments by the combination of a rigid material embedded within a flexible material. The rigid struts and/or plates may comprise polyimide, prolene or any derivative of nylon, PMMA titanium or other rigid or inert material, or a combination of rigid and flexible materials to make the haptics rigid longitudinally.

As used herein, the relative terms "proximal" and "distal" shall be defined from the perspective of the optic. Thus, proximal refers to the direction toward the optic, and distal refers to the direction away from the optic.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Although certain embodiments and examples have been described herein, it will be understood by those skilled in the art that many aspects of the intraocular lenses shown and described in the present disclosure may be differently combined and/or modified to form still further embodiments or acceptable examples. The theory of the operation disclosed herein is the best understanding of the operation of the devices disclosed and claimed, but is not to be considered limiting with regard to the claimed subject matter. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

The invention claimed is:

1. An intraocular lens comprising:
   a flexible optic configured to be vaulted posteriorly in the eye after insertion; and
   a pair of haptics connected to the optic, each haptic comprising a proximal end and a distal end, the proximal end being closer to the optic than the distal end, each haptic comprising a single and separate rigid structure at least partially embedded in a flexible material and having a fixed length;
   wherein each rigid structure comprises:
      a pair of plate portions extending in a longitudinal direction;
      at least one loop extending from each plate portion, at least a portion of the loop extending beyond a distal end of the flexible material such that fibrosis can fix the rigid structure within the capsular bag; and
      at least one transverse bar extending between the two plate portions to form a central, enclosed, open region positioned between the plate portions,
   wherein a thickness of each said at least one transverse bar measured along or parallel to the longitudinal axis of the intraocular lens is sufficiently thin to enable the intraocular lens to be folded about an axis along or parallel to the longitudinal axis of the intraocular lens;
   wherein the intraocular lens has a uniplanar configuration and a posterior vaulted configuration, the intraocular lens being configured to transition from the uniplanar configuration to the posterior vaulted configuration after implantation;
   wherein the length of each of the rigid structure is the same in the uniplanar configuration and the posterior vaulted configuration; and
   wherein the pair of haptics are capable of resisting bending from pressure exerted on the distal ends of the haptics by contraction of the ciliary muscle and fibrosis to generally leave the optic in the same position along an optical axis of the eye when the intraocular lens is positioned in the capsular bag.

2. The intraocular lens of claim 1, wherein each haptic is foldable about a longitudinal axis of the haptic.

3. The intraocular lens of claim 1, wherein a longitudinal dimension of the intraocular lens is between about 9.5 mm and about 12.0 mm.

4. The intraocular lens of claim 1, wherein the rigid structure is connected to the flexible optic by a short extension of the flexible optic.

5. The intraocular lens of claim 1, wherein the flexible material and the optic comprise the same material.

6. The intraocular lens of claim 1, wherein the flexible material comprises silicone or acrylic.

7. The intraocular lens of claim 1, wherein said at least one loop is a closed loop.

8. The intraocular lens of claim 1, wherein said at least one loop is an open loop.

9. The intraocular lens of claim 1, wherein the loop structure has a width that is less than the width of one of the plate portions.

10. The intraocular lens of claim 1, wherein the rigid structure comprises extensions at a distal end thereof.

11. The intraocular lens of claim 1, wherein said at least one transverse bar is disposed at a distal end of its respective rigid structure.

12. The intraocular lens of claim 1, wherein at least one haptic is connected to the flexible optic by a short extension.

13. An intraocular lens comprising:
a flexible optic configured to be vaulted posteriorly in the eye after insertion in the eye, and
a pair of haptics connected to the optic, each haptic comprising a proximal end and a distal end, the proximal end being closer to the optic than the distal end, each haptic comprising:
a rigid structure at least partially embedded in a flexible material, said rigid structure comprising a plurality of loops, a portion of each loop extending beyond a distal end of the flexible material such that fibrosis can fix the rigid structure within the capsular bag;
wherein the intraocular lens comprises a uniplanar configuration and a posterior vaulted configuration, the intraocular lens being configured to transition from the uniplanar configuration to the posterior vaulted configuration after implantation;
wherein a length of each rigid structure is the same in the uniplanar configuration and the posterior vaulted configuration; and
wherein the pair of plate haptics are resistant to bending from pressure exerted on the distal ends of the haptics by contraction of the ciliary muscle and fibrosis to generally leave the optic in the same position along an optical axis of the eye when the intraocular lens is positioned in the capsular bag.

14. The intraocular lens of claim 13, wherein each haptic is foldable about a longitudinal axis of the haptic.

15. The intraocular lens of claim 13, wherein said loops are closed loops.

16. The intraocular lens of claim 13, wherein said loops are open loops.

17. The intraocular lens of claim 13, wherein the flexible material and the optic comprise the same material.

18. The intraocular lens of claim 13, wherein the flexible material comprises silicone or acrylic.

19. An intraocular lens comprising:
a flexible optic configured to be vaulted posteriorly in the eye after insertion; and
a pair of haptics connected to the optic, each haptic comprising a proximal end and a distal end, the proximal end being closer to the optic than the distal end, each haptic comprising a rigid structure comprising a plurality of loops such that fibrosis can fix the rigid structure within the capsular bag;
wherein the intraocular lens comprises a uniplanar configuration and a posterior vaulted configuration, the intraocular lens being configured to transition from the uniplanar configuration to the posterior vaulted configuration after implantation;
wherein each rigid structure has a fixed length in the uniplanar configuration and the posterior vaulted configuration; and
wherein the pair of haptics are resistant to bending from pressure exerted on the distal ends of the haptics by contraction of the ciliary muscle and fibrosis to generally leave the optic in the same position along an optical axis of the eye when the intraocular lens is positioned in the capsular bag.

20. The intraocular lens of claim 19, wherein each haptic is foldable about a longitudinal axis of the haptic.

21. The intraocular lens of claim 19, wherein said loops are closed loops.

22. The intraocular lens of claim 19, wherein said loops are open loops.

23. The intraocular lens of claim 19, wherein said intraocular lens is monolithic.

24. The intraocular lens of claim 19, wherein the flexible optic and each haptic comprise the same material.

25. The intraocular lens of claim 24, wherein the same material is acrylic.

26. The intraocular lens of claim 1, wherein said lens is non-accommodating.

27. The intraocular lens of claim 13, wherein said lens is non-accommodating.

28. The intraocular lens of claim 19, wherein said lens is non-accommodating.

* * * * *